(12) United States Patent
Renye, Jr. et al.

(10) Patent No.: US 9,598,471 B2
(45) Date of Patent: Mar. 21, 2017

(54) BACTERIOCIN WITH NOVEL ACTIVITY

(71) Applicant: The United States of America, as represented by the Secretary of Agriculture, Washington, DC (US)

(72) Inventors: John A Renye, Jr., North Wales, PA (US); George A Somkuti, Lansdale, PA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 14/743,024

(22) Filed: Jun. 18, 2015

(65) Prior Publication Data
US 2016/0368953 A1 Dec. 22, 2016

(51) Int. Cl.
*C07K 14/315* (2006.01)
*A01N 63/02* (2006.01)
*A61K 38/00* (2006.01)

(52) U.S. Cl.
CPC .......... *C07K 14/315* (2013.01); *A01N 63/02* (2013.01); *A61K 38/00* (2013.01); *C07K 2319/00* (2013.01)

(58) Field of Classification Search
CPC .. C07K 14/315; C07K 2319/00; A01N 63/02; A61K 38/00
See application file for complete search history.

(56) References Cited

U.S. PATENT DOCUMENTS

| | | | | |
|---|---|---|---|---|
| 2006/0229244 A1* | 10/2006 | Dorit | ............... | A61K 38/164 514/2.8 |
| 2010/0092526 A1* | 4/2010 | Baker, Jr. | ............ | A61K 9/1075 424/400 |
| 2010/0166721 A1* | 7/2010 | Masri | ................. | A23C 9/123 424/93.44 |

OTHER PUBLICATIONS

Mehta et al., Guidelines for prevention of hospital acquired infections, Indian J Crit Care Med. Mar. 2014; 18(3): 149-163, supplied as a 23-page PDF document.*
Gilbreth and Somkuti, Thermophilin 110: A Bacteriocin of *Streptococcus thermophilis* ST 110, Current Microb. vol. 51, (2005) pp. 175-182.*
Hurley and Thiel, Perspectives on Immunoglobulins in Colostrum and Milk, Nutrients 2011, 3, 442-474.*
Rodriguez et al., Diversity of bacteriocins produced by lactic acid bacteria isolated from raw milk, International Dairy Journal 10 (2000) 7-15.*
Gilbreth and Somkuti, Thermophilin 110: A Bacteriocin of *Streptococcus thermophilis* ST 110, Current Microb. vol. 51, (2005) pp. 175-180.*

Blomqvist, Trinelise et al., "Pheromone-induced expression of recombinant proteins in *Streptococcus thermophilus*" (2006) Arch Microbiology 186:465-473.
Bolotin, Alexander et al., "Complete sequence and comparative genome analysis of the dairy bacterium *Streptococcus thermophilus*", (2004) Nature Biotechnology 22(12):1554-1558.
De Saizieu, Antoine et al., "Microarray-Based Identification of a Novel *Streptococcus pneumoniae* Regulon Controlled by an Autoinduced Peptide", (2000) Journal of Bacteriology 182(17):4696-4703.
Fontaine, Laetitia et al., "Quorum-Sensing Regulation of the Production of Blp Bacteriocins in *Streptococcus thermophilus*", (2007) Journal of Bacteriology 189(20):7195-7205.
Fontaine, Laetitia et al., "The Inhibitory Spectrum of Thermophilin 9 from *Streptococcus thermophilus* LMD-9 Depends on the Production of Multiple Peptides and the Activity of BlpGSt, a Thiol-Disulfide Oxidase", (2008) Applied and Environmental Microbiology 74(4):1102-1110.
Gilbreth, Stephanie et al., "Thermophilin 110: A Bacteriocin of *Streptococcus thermophilus* ST110", (2005) Current Microbiology 51:175-182.
Hols, Pascal et al., "New insights in the molecular biology and physiology of *Streptococcus thermophilus* revealed by comparative genomics", (2005) FEMS Microbiology Reviews 29:435-463.
Ivanova, I. et al., "Characterization of a bacteriocin produced by *Streptococcus thermophilus* 81", (1998) International Journal of Food Microbiology 42:147-158.
Kabuki, T. et al., "Characterization of a bacteriocin, Thermophilin 1277, produced by *Streptococcus thermophilus* SBT1277", (2007) Journal of Applied Microbiology 102:971-980.
Kang, Xiaohong et al., "Complete Genome Sequence of *Streptococcus thermophilus* Strain MN-ZLW-002", (2012) Journal of Bacteriology 194(16):4428-4429.
Khalil, Rowaida, "Evidence for Probiotic Potential of a Capsular-Producing *Streptococcus thermophilus* CHCC 3534 Strain", (2009) Polish Journal of Microbiology 58(1):49-55.
Lamy, Marie-Cecile et al., "CovS/CovR of group B streptococcus: a two-component global regulatory system involved in virulence", (2004) Molecular Microbiology 54(5):1250-1268.
Marciset, Olivier et al., "Thermophilin 13, a Nontypical Antilisterial Poration Complex Bacteriocin, That Functions without a Receptor", (1997) Journal of Biological Chemistry 272(22):14277-14284.
Mathot, A. G. et al., "*Streptococcus thermophilus* 580 Produces a Bacteriocin Potentially Suitable for Inhibition of Clostridium tyrobutyricum in Hard Cheese", (2003) Journal of Dairy Science 86:3068-3074.
Renye, John A. et al., "BlpC-regulated bacteriocin production in *Streptococcus thermophilus*", (2013) Biotechnology Letters 35:407-412.

(Continued)

*Primary Examiner* — Lianko Garyu
*Assistant Examiner* — Joseph Fischer
(74) *Attorney, Agent, or Firm* — John D. Fado; Ariel A. Atkinson

(57) ABSTRACT

A bacteriocin produced constitutively by *Streptococcus thermophilus* strain 110 (NRRL B59671), thermophilin 110, kills and/or inhibits the growth *Streptococcus pyogenes*, *Streptococcus mutans*, and/or *Propionibacterium acnes*. Thermophilin 110 is the first bacteriocin identified with this activity. Thus, compositions containing thermophilin 110 and/or *Streptococcus thermophilus* strain 110 (NRRL B59671) can be used to prevent and/or treat diseases caused by *Streptococcus pyogenes*, *Streptococcus mutans*, and/or *Propionibacterium acnes*. Such diseases include strep throat, dental caries, and acne, respectively. Methods to inhibit the growth of these bacteria and/or treat the diseases are also included.

3 Claims, 6 Drawing Sheets

(56) References Cited

OTHER PUBLICATIONS

Rossi, Franca et al., "Diversity of *Streptococcus thermophilus* in bacteriocin production; inhibitory spectrum and occurrence of thermophilin genes", (2013) Food Microbiology 35:27-33.

Sun, Zhihong et al., "Complete Genome Sequence of *Streptococcus thermophilus* Strain ND03", (2011) Journal of Bacteriology 193(3):793-794.

Villani, F. et al., "Antilisterial activity of thermophilin 347, a bacteriocin produced by *Streptococcus thermophilus*", (1994) International Journal of Food Microbiology 25:179-190.

Ward, D.J. et al., "Characterization of a bacteriocin produced by *Streptococcus thermophilus* ST134", (1995) Applied Microbiology and Biotechnology 43:330-335.

* cited by examiner

SEQUENCE LISTING

<160> NUMBER OF SEQ ID NOS: 38

<210> SEQ ID NO 1
<211> LENGTH: 76
<212> TYPE: PRT
<213> ORGANISM: Streptococcus thermophilus

<400> SEQUENCE: 1

```
Met Ala Thr Gln Thr Ile Glu Asn Phe Asn Thr Leu Asp Leu Glu Thr
1               5                   10                  15
Leu Ala Ser Val Glu Gly Gly Cys Ser Trp Gly Gly Phe Ala Lys
            20                  25                  30
Gln Gly Val Ala Thr Gly Val Gly Asn Gly Leu Arg Leu Gly Ile Lys
        35                  40                  45
Thr Arg Thr Trp Gln Gly Ala Val Ala Gly Ala Ala Gly Gly Ala Ile
    50                  55                  60
Val Gly Gly Val Gly Tyr Gly Ala Thr Cys Trp Trp
65                  70                  75
```

<210> SEQ ID NO 2
<211> LENGTH: 231
<212> TYPE: DNA
<213> ORGANISM: Streptococcus thermophilus

<400> SEQUENCE: 2

```
atggcaactc aaacaattga aaactttaac acccttgacc tcgaaacact tgctagtgtt    60
gaaggtggtg atgtagctgg gggaggtttt gctaaacaag gagtagctac aggagttggt   120
aatggtttac gactaggtat caaaacacgt acttggcaag gtgctgtcgc aggagcagct   180
ggaggtgcta tcgtaggtgg tgttggttat ggagcaacat gctggtggtg a             231
```

<210> SEQ ID NO 3
<211> LENGTH: 18
<212> TYPE: DNA
<213> ORGANISM: Streptococcus thermophilus

<400> SEQUENCE: 3

```
atgtttcgtt ttcgtagg                                                   18
```

<210> SEQ ID NO 4
<211> LENGTH: 18
<212> TYPE: DNA
<213> ORGANISM: Streptococcus thermophilus

<400> SEQUENCE: 4

```
aatttttacg attcattt                                                   18
```

<210> SEQ ID NO 5
<211> LENGTH: 13
<212> TYPE: DNA
<213> ORGANISM: Streptococcus thermophilus

<400> SEQUENCE: 5

```
accgtttggg acg                                                        13
```

<210> SEQ ID NO 6
<211> LENGTH: 13
<212> TYPE: DNA
<213> ORGANISM: Streptococcus thermophilus

<400> SEQUENCE: 6 acttttggg acg          13

<210> SEQ ID NO 7
<211> LENGTH: 13
<212> TYPE: DNA
<213> ORGANISM: Streptococcus thermophilus

<400> SEQUENCE: 7
accattcggg aca          13

<210> SEQ ID NO 8
<211> LENGTH: 13
<212> TYPE: DNA
<213> ORGANISM: Streptococcus thermophilus

<400> SEQUENCE: 8
actactcggg aca          13

<210> SEQ ID NO 9
<211> LENGTH: 16
<212> TYPE: DNA
<213> ORGANISM: Streptococcus thermophilus

<400> SEQUENCE: 9
caatttttca ataaac          16

<210> SEQ ID NO 10
<211> LENGTH: 17
<212> TYPE: DNA
<213> ORGANISM: Streptococcus thermophilus

<400> SEQUENCE: 10
cctacgggag gcagcag          17

<210> SEQ ID NO 11
<211> LENGTH: 17
<212> TYPE: DNA
<213> ORGANISM: Streptococcus thermophilus

<400> SEQUENCE: 11
attaccgcgg ctgctgg          17

<210> SEQ ID NO 12
<211> LENGTH: 18
<212> TYPE: DNA
<213> ORGANISM: Streptococcus thermophilus

<400> SEQUENCE: 12
ggctaacaat acgattaa          18

<210> SEQ ID NO 13
<211> LENGTH: 18
<212> TYPE: DNA
<213> ORGANISM: Streptococcus thermophilus

<400> SEQUENCE: 13
gcttgaggaa tgttatag          18

<210> SEQ ID NO 14
<211> LENGTH: 18
<212> TYPE: DNA
<213> ORGANISM: Streptococcus thermophilus

<400> SEQUENCE: 14

```
ccaccagcat gttgctcc                                                   18

<210> SEQ ID NO 15
<211> LENGTH: 20
<212> TYPE: DNA
<213> ORGANISM: Streptococcus thermophilus

<400> SEQUENCE: 15
gctaaacaag gagtagctac                                                 20

<210> SEQ ID NO 16
<211> LENGTH: 20
<212> TYPE: DNA
<213> ORGANISM: Streptococcus thermophilus

<400> SEQUENCE: 16
cctgcaccac ctagaacacc                                                 20

<210> SEQ ID NO 17
<211> LENGTH: 20
<212> TYPE: DNA
<213> ORGANISM: Streptococcus thermophilus

<400> SEQUENCE: 17
cacccttgac ctcgaaacac                                                 20

<210> SEQ ID NO 18
<211> LENGTH: 18
<212> TYPE: DNA
<213> ORGANISM: Streptococcus thermophilus

<400> SEQUENCE: 18
gaaacagtat aaggctgc                                                   18

<210> SEQ ID NO 19
<211> LENGTH: 18
<212> TYPE: DNA
<213> ORGANISM: Streptococcus thermophilus

<400> SEQUENCE: 19
ggttgtcctg tgatgagg                                                   18

<210> SEQ ID NO 20
<211> LENGTH: 21
<212> TYPE: DNA
<213> ORGANISM: Streptococcus thermophilus

<400> SEQUENCE: 20
aaacaccatg ttcacctcca g                                               21

<210> SEQ ID NO 21
<211> LENGTH: 18
<212> TYPE: DNA
<213> ORGANISM: Streptococcus thermophilus

<400> SEQUENCE: 21
ccgatggcat gggtagag                                                   18

<210> SEQ ID NO 22
<211> LENGTH: 21
<212> TYPE: DNA
<213> ORGANISM: Streptococcus thermophilus
```

```
<400> SEQUENCE: 22
tcgtgaaatg attcaaggac a                                     21

<210> SEQ ID NO 23
<211> LENGTH: 24
<212> TYPE: DNA
<213> ORGANISM: Streptococcus thermophilus

<400> SEQUENCE: 23
tcgtgtctaa aactacgaac agaa                                  24

<210> SEQ ID NO 24
<211> LENGTH: 27
<212> TYPE: DNA
<213> ORGANISM: Streptococcus thermophilus

<400> SEQUENCE: 24
cccactagtc gctaagggct tacttga                               27

<210> SEQ ID NO 25
<211> LENGTH: 27
<212> TYPE: DNA
<213> ORGANISM: Streptococcus thermophilus

<400> SEQUENCE: 25
cccctgcagg gaaatcttcc tctaatt                               27

<210> SEQ ID NO 26
<211> LENGTH: 27
<212> TYPE: DNA
<213> ORGANISM: Streptococcus thermophilus

<400> SEQUENCE: 26
cccctcgagg ctttgttagg taatatc                               27

<210> SEQ ID NO 27
<211> LENGTH: 29
<212> TYPE: DNA
<213> ORGANISM: Streptococcus thermophilus

<400> SEQUENCE: 27
cccggtaccg aggacaacat tctcaatcg                             29

<210> SEQ ID NO 28
<211> LENGTH: 27
<212> TYPE: DNA
<213> ORGANISM: Artificial Sequence
<220> FEATURE:
<223> OTHER INFORMATION: PRIMER

<400> SEQUENCE: 28
cccggtaccg gaaaaaatac ctcagac                               27

<210> SEQ ID NO 29
<211> LENGTH: 29
<212> TYPE: DNA
<213> ORGANISM: Artificial Sequence
<220> FEATURE:
<223> OTHER INFORMATION: PRIMER

<400> SEQUENCE: 29
cccctcgagt cctaatgtat attatttct                             29
```

```
<210> SEQ ID NO 30
<211> LENGTH: 29
<212> TYPE: DNA
<213> ORGANISM: Artificial Sequence
<220> FEATURE:
<223> OTHER INFORMATION: PRIMER

<400> SEQUENCE: 30
cccctgcagg gctgttatga gttttttag                              29

<210> SEQ ID NO 31
<211> LENGTH: 27
<212> TYPE: DNA
<213> ORGANISM: Artificial Sequence
<220> FEATURE:
<223> OTHER INFORMATION: PRIMER

<400> SEQUENCE: 31
cccactagtc caacgcagca gtgatgg                                27

<210> SEQ ID NO 32
<211> LENGTH: 28
<212> TYPE: DNA
<213> ORGANISM: Artificial Sequence
<220> FEATURE:
<223> OTHER INFORMATION: PRIMER

<400> SEQUENCE: 32
cccctgcagg gaagatttcc aatgattg                               28

<210> SEQ ID NO 33
<211> LENGTH: 27
<212> TYPE: DNA
<213> ORGANISM: Artificial Sequence
<220> FEATURE:
<223> OTHER INFORMATION: PRIMER

<400> SEQUENCE: 33
cccactagtg gtgtacagat gtgactt                                27

<210> SEQ ID NO 34
<211> LENGTH: 39
<212> TYPE: DNA
<213> ORGANISM: Artificial Sequence
<220> FEATURE:
<223> OTHER INFORMATION: PRIMER

<400> SEQUENCE: 34
ataggatcca tcgaaggtcg tggatgtagc tggggaggt                   39

<210> SEQ ID NO 35
<211> LENGTH: 28
<212> TYPE: DNA
<213> ORGANISM: Artificial Sequence
<220> FEATURE:
<223> OTHER INFORMATION: PRIMER

<400> SEQUENCE: 35
atctcgagtc accaccagca tgttgctc                               28

<210> SEQ ID NO 36
<211> LENGTH: 53
<212> TYPE: PRT
<213> ORGANISM: Streptococcus thermophilus

<400> SEQUENCE: 36
```

-continued

```
Gly Cys Ser Trp Gly Gly Phe Ala Lys Gln Gly Val Ala Thr Gly Val
1               5                   10                  15

Gly Asn Gly Leu Arg Leu Gly Ile Lys Thr Arg Thr Trp Gln Gly Ala
            20                  25                  30

Val Ala Gly Ala Ala Gly Gly Ala Ile Val Gly Gly Val Gly Tyr Gly
            35                  40                  45

Ala Thr Cys Trp Trp
            50

<210> SEQ ID NO 37
<211> LENGTH: 162
<212> TYPE: DNA
<213> ORGANISM: Streptococcus thermophilus

<400> SEQUENCE: 37
ggatgtagct ggggaggttt tgctaaacaa ggagtagcta caggagttgg taatggttta      60
cgactaggta tcaaaacacg tacttggcaa ggtgctgtcg caggagcagc tggaggtgct     120
atcgtaggtg gtgttggtta tggagcaaca tgctggtggt ga                        162

<210> SEQ ID NO 38
<211> LENGTH: 23
<212> TYPE: PRT
<213> ORGANISM: Streptococcus thermophilus

<400> SEQUENCE: 38

Met Ala Thr Gln Thr Ile Glu Asn Phe Asn Thr Leu Asp Leu Glu Thr
1               5                   10                  15

Leu Ala Ser Val Glu Gly Gly
            20
```

BACTERIOCIN WITH NOVEL ACTIVITY

BACKGROUND OF THE INVENTION

Summary of the Invention

This invention relates to a novel use for a bacteriocin and/or the bacteria that produces this bacteriocin. The novel use involving killing *Streptococcus pyogenes, Streptococcus mutans*, and/or *Propionibacterium acnes*, and preventing or treating diseases caused by these bacteria. This invention also relates to compositions containing this bacteriocin and/or the bacteria that produce this bacteriocin useful in preventing or treating diseases caused by *S. pyogenes, S. mutans*, and/or *P. acnes* and killing *S. pyogenes, S. mutans*, and/or *P. acnes*.

Summary of the Prior Art

*Streptococcus thermophilus* is a thermophilic lactic acid bacteria commonly used as a starter culture in the production of yogurt and cheeses. Several strains of *S. thermophilus* have been reported to naturally produce antimicrobial peptides called bacteriocins. These ribosomally encoded peptides have been shown to display a narrow and/or broad spectrum of activity with the potential to inhibit the growth of spoilage and food-borne pathogenic bacteria (Villani, et al., *Int. J. Food Microbiol.* 25, 179-90 (1995); Ward & Somkuti, *Appl. Microbiol. Biotechnol.* 43, 330-5 (1995); Marciset, et al., *J. Biol. Chem.* 272, 14277-84 (1997); Ivanova, et al., *Int. J. Food Microbiol.* 42, 147-58 (1998); Mathot, et al., *J. Dairy Sci.* 86, 3068-74 (2003); Gilbreth & Somkuti, *Curr. Microbiol.* 51, 175-82 (2005); Kabuki, et al., *J. Appl. Microbiol.* 102, 971-80 (2007); Khalil, *Pol. J. Microbiol.* 58, 49-55 (2009); Rossi, et al., *Food Microbiol.* 35, 27-33 (2013)). The genes encoding these bacteriocins have been identified for thermophilin 13, a two component bacteriocin (Marciset, et al. (1997)), and the lantibiotic thermophilin 1277 (Kabuki, et al. (2007)); but remain uncharacterized in other *S. thermophilus* strains.

Comparative genomic studies on *S. thermophilus* strains LMD-9, CNRZ1066 and LMG18311 (Hols, et al., *FEMS Microbiol. Rev.* 29, 435-63 (2005)), which were initially thought to not produce a bacteriocin, revealed the presence of a gene cluster resembling the class II bacteriocin-like peptide locus in *Streptococcus pneumoniae* (de Saizieu, et al., *J. Bacteriol.* 182, 4696-703 (2000)). Each *S. thermophilus* strain was shown to contain a three gene operon (blpABC) that encoded the components of an ABC-transporter (blpAB) required for processing and secretion of a quorum-sensing induction peptide (QSIP), encoded by blpC. The QSIP was initially expressed as a 53 residue prepeptide and further processed to the mature 30-mer QSIP by removal of a 23 amino acid leader peptide (Fontaine, et al., *J. Bacteriol.* 189, 7195-205 (2007)). Immediately downstream of blpABC, was a two gene operon (blpRH) that encoded a histidine kinase (BlpH) and response regulator (BlpR) required for sensing the QSIP and inducing the expression of other genes within the cluster (Blomqvist, et al., *Arch. Microbiol.* 186, 465-73 (2006)). The remaining components of each gene cluster differed significantly with *S. thermophilus* strains LMD-9, LMG18311 and CNRZ1066 possessing 15, 12 and 4 genes respectively. Within this region were the genes believed to encode the actual bacteriocins based on the presence of a double glycine leader sequence and included blpD, blpU, blpE and blpF in *S. thermophilus* strain LMD-9; blpU and blpK in *S. thermophilus* strain LMG18311 and blpK in *S. thermophilus* strain CNRZ1066 (Hols, et al. (2005)). In *S. thermophilus* strain LMD-9, the addition of synthetic QSIP to the growth medium resulted in the expression of a broad spectrum bacteriocin (Fontaine, et al. (2007)), but it failed to induce bacteriocin production in *S. thermophilus* strains LMG81311 and CNRZ1066. The inability of these two strains to produce an active bacteriocin was thought to result from a truncation in BlpB which is required for the secretion of the antimicrobial peptides (Hols, et al. (2005)). Further analysis of *S. thermophilus* strain LMD-9 revealed that BlpD alone was sufficient to inhibit the growth of most target bacteria, thus BlpU, BlpE, BlpF were classified as accessory peptides (Fontaine & Hols, *Appl. Environ. Microbiol.* 74, 1102-10 (2008)). In *S. thermophilus* strain LMD-9, a thiol-disulfide oxidase encoded by blpG was identified, and shown to be essential for the strain's novel anti-listerial activity (Fontaine & Hols (2008)). Additional variations within this gene cluster have been reported in other *S. thermophilus* strains (Rossi, et al. (2013)), and the potential for identifying new variants increases as more *S. thermophilus* genomes are fully sequenced.

Previously, the natural production of an anti-pediococcal bacteriocin, thermophilin 110, by *S. thermophilus* strain 110 (USDA, ARS NRRL patent depository accession number B59671) (hereinafter referred to as "*S. thermophilus* strain 110 (NRRL B59671)") was described (Gilbreth & Somkuti (2005)). Another study reported that thermophilin 110 production was regulated by BlpC (Renye & Somkuti, *Biotechnol. Lett.* 35, 407-12 (2013)).

Herein, it is demonstrated that pro-thermophilin 110 produced by *S. thermophilus* strain 110 (NRRL B59671) is encoded by blpU. The pro-thermophilin 110, also referred to as BlpU, has the amino acid sequence of SEQ ID NO: 1. This sequence includes a 23 amino acid leader sequence (SEQ ID NO: 38; amino acids 1-23 of SEQ ID NO: 1) that is cleaved off during translation or post-translational processing. The amino acid sequence of mature thermophilin 110 protein is in SEQ ID NO: 36 and is also amino acids 24-76 of SEQ ID NO: 1. The DNA sequence for blpU is in SEQ ID NO: 2 which includes nucleotides 1-69 that encode for the 23 amino acid leader sequence peptide. The DNA sequence of the mature thermophilin 110 protein is in SEQ ID NO: 37 and is also nucleotides 70-228 of SEQ ID NO: 2. As demonstrated infra, mature thermophilin 110 has anti-bacterial activity. Pro-thermophilin 110 lacks anti-bacterial activity. As such, when used herein, "thermophilin 110" refers to mature thermophilin 110 (amino acids 24-76 of SEQ ID NO: 1 which is the same as all of SEQ ID NO: 36), unless the context clearly indicates the pro-thermophilin 110 form.

Also demonstrated herein, thermophilin 110 has anti-bacterial activity against *S. pyogenes, S. mutans*, and *P. acnes*; this anti-bacterial activity being novel and unknown prior to the studies reported herein. Furthermore, no other bacteriocin made by *S. thermophilus* has exhibited bactericidal activity against *S. pyogenes, S. mutans*, and *P. acnes*. *S. thermophilus* strain 110 (NRRL B59671) can be used a probiotic composition to prevent the growth of and/or kill *S. pyogenes, S. mutans*, and *P. acnes*, and thus prevent, reduce the symptoms of, and/or treat the diseases caused by these bacteria, namely strep throat, dental caries, and acne, respectively. *P. acnes* is also suspected to be involved in post-operative infections, prostheses failure, and in inflammation of lumbar nerve roots leading to sciatica.

BRIEF DESCRIPTION OF THE INVENTION

It is an object of this invention to have an isolated and purified bacteriocin (referred to as thermophilin) produced by *Streptococcus thermophilus* strain 110 (NRRL B59671) and that thermophilin 110 contains amino acids 24-76 of SEQ ID NO: 1. It is a further object of this invention that pro-thermophilin 110 has a DNA sequence of SEQ ID NO: 2 and that mature thermophilin 110 has the DNA sequence of SEQ ID NO: 37.

It is another object of this invention to have an anti-bacterial composition containing a carrier and concentrated or purified thermophilin 110, *Streptococcus thermophilus* strain 110 (NRRL B59671), or a combination of both. The carrier can be a pharmaceutically acceptable carrier, a veterinarian acceptable carrier, an orally acceptable carrier, a dermatologically acceptable carrier, and a disinfectant carrier.

It is another object of this invention to have a method killing bacteria on a surface comprising applying an anti-bacterial composition to the surface in an amount effective to kill the bacteria. The anti-bacterial composition contains a carrier and an anti-bacterial agent which can be purified or concentrated thermophilin 110, *Streptococcus thermophilus* strain 110 (NRRL B59671), or a combination of both. The bacteria includes *Streptococcus pyogenes, Streptococcus mutans*, and *Propionibacterium acnes*. The carrier can be a pharmaceutically acceptable carrier, a veterinarian acceptable carrier, an orally acceptable carrier, a dermatologically acceptable carrier, and a disinfectant carrier. The anti-bacterial composition can be applied to the surface of an animal's tissue, medical equipment, or any other surface that needs disinfecting.

It is further object of this invention to have a method of treating bacterial infection in an animal in need of treatment by administering an anti-bacterial composition to the animal in an amount effective to treat the infection. The anti-bacterial composition contains a carrier and an anti-bacterial agent which can be concentrated or purified thermophilin 110, *Streptococcus thermophilus* strain 110 (NRRL B59671), or a combination thereof. The bacteria includes *Streptococcus pyogenes, Streptococcus mutans*, and *Propionibacterium acnes*. The carrier can be a pharmaceutically acceptable carrier, a veterinarian acceptable carrier, an orally acceptable carrier, a dermatologically acceptable carrier, and a disinfectant carrier. The anti-bacterial composition can be applied to the animal's hide or skin or administer internally.

It is an object of this invention to have a method of inhibiting the growth of bacteria in or on an animal by administering an anti-bacterial composition to the animal in an amount effective to kill the bacteria. The anti-bacterial composition contains a carrier and an anti-bacterial agent which can be concentrated or purified thermophilin 110, *Streptococcus thermophilus* strain 110 (NRRL B59671), or a combination thereof. The bacteria includes *Streptococcus pyogenes, Streptococcus mutans*, and *Propionibacterium acnes*. The carrier can be a pharmaceutically acceptable carrier, a veterinarian acceptable carrier, an orally acceptable carrier, a dermatologically acceptable carrier, and a disinfectant carrier. The anti-bacterial composition can be applied to the animal's hide or skin or administer internally.

It is an object of this invention to have a polynucleotide encoding mature thermophilin 110 (SEQ ID NO: 36). It is another object to have a polynucleotide encoding a fusion protein that is a combination of thermophilin 110 and a heterologous polypeptide or protein. The polynucleotide encoding thermophilin 110 is operably linked to the polynucleotide encoding the heterologous polypeptide. It is a further object of this invention that one can process the fusion protein to separate thermophilin 110 from the heterologous polypeptide. The fusion protein can contain amino acids that are the recognition sequence for enzymatic cleavage or other form to separate thermophilin 110 from the heterologous polypeptide. It is a further object of this invention that the released thermophilin 110 can be concentrated and/or purified. It is another object of this invention to have an expression vector containing a polynucleotide encoding this fusion protein operably linked to a promoter. It is further object of this invention to have a recombinant organism that contains this expression vector. The recombinant organism can be a bacterium, a yeast, plant, or animal. It is further object of this invention to produce and isolate the fusion protein so that one can purify and/or concentrate thermophilin 110.

mRNA expression of blpR and blpH in a non-induced *S. thermophilus* strain LMD-9 culture (no QSIP) is used as the base line level. Data are the average of at least three independent experiments (±standard deviation).

Figure 6:
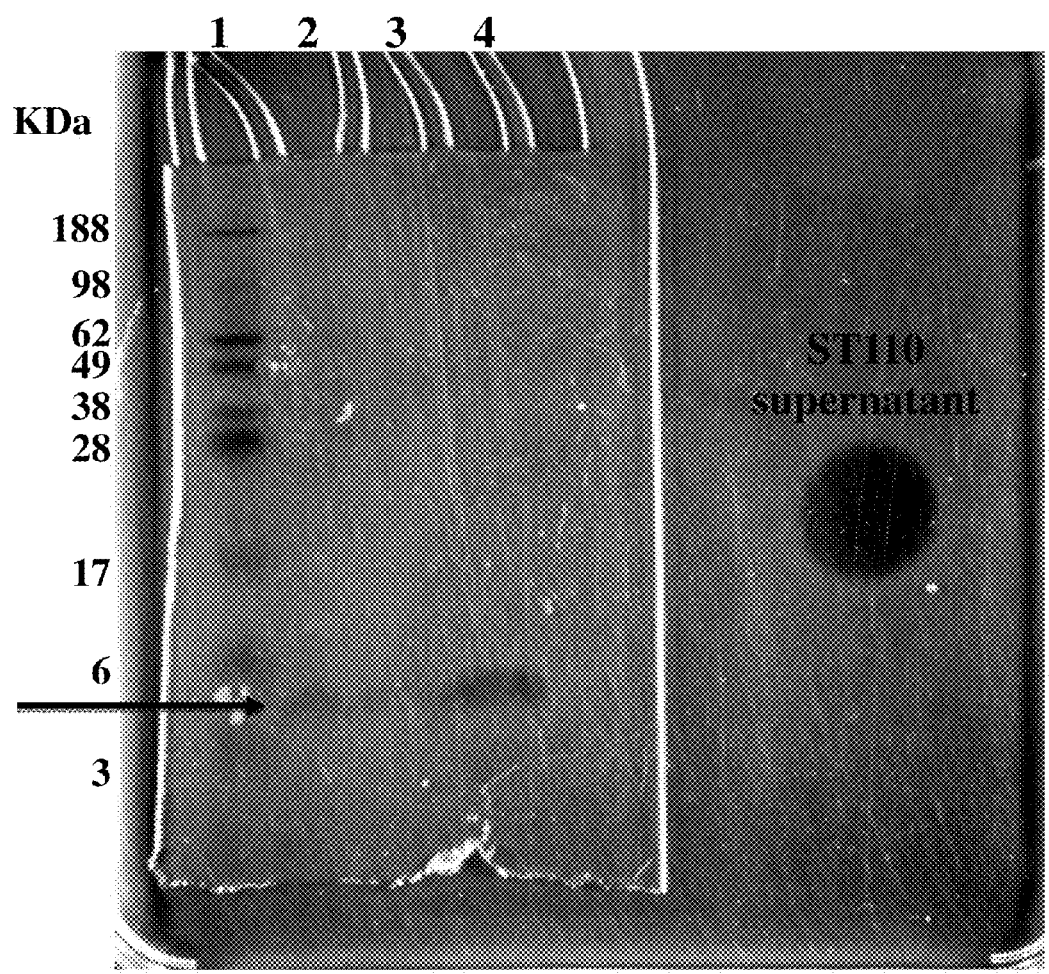

FIG. 6 is a photograph of an agar plate inoculated with *P. acidilactici* and, on the left, overlaid with SDS-PAGE gel containing markers in lane 1, 30 µl of BlpU expressed in *E. coli* BL21 containing pGEX-6P-1/blpU and cleaved with Factor Xa protease in lane 2, 10 µl of *S. thermophilus* strain 110 (NRRL B59671) supernatant in lane 3, and 30 µl of *S. thermophilus* strain 110 (NRRL B59671) supernatant in lane 4. On the right side of the agar plate, 5 µl of *S. thermophilus* strain 110 (NRRL B59671) supernatant is spotted directly onto the agar plate. The arrow on the left side of FIG. 6 shows the inhibition zone of the bacteriocin run on the SDS-PAGE gel.

DECLARATION REGARDING DEPOSIT OF BIOLOGICAL MATERIALS UNDER THE BUDAPEST TREATY

On Dec. 2, 2011, we, the inventors of the invention described herein, affirm that we deposited two samples of *Streptococcus thermophilus* strain 110 with the U.S.D.A., Agricultural Research Service's Patent Culture Collection located at the National Center for Agricultural Utilization Research, 1815 N. University Street, Peoria, Ill. 61604, in a manner affording permanence of the deposits and ready accessibility thereto by the public if a patent is granted. *S. thermophilus* strain 110 was accorded deposit number NRRL B59671. This deposit was made under the terms of the Budapest Treaty on the International Recognition of the Deposit of Microorganisms for the Purposes of Patent Procedure and the regulations thereunder.

All restrictions on the availability to the public of *S. thermophilus* strain 110 ARS's Patent Culture Collection Accession Number NRRL B59671 will be irrevocably removed upon the granting of a patent.

*S. thermophilus* strain 110 ARS's Patent Culture Collection Accession Number NRRL B59671 was deposited under conditions such that access to the microorganism is available during the pendency of the patent application to one determined by the Commissioner to be entitled thereto under 37 C.F.R. §1.14 and 35 U.S.C §122.

The deposited biological material will be maintained with all the care necessary to keep them viable and uncontaminated for a period of at least five years after the most recent request for the furnishing of a sample of the deposited microorganism, and in any case, for a period of at least thirty (30) years after the date of deposit or for the enforceable life of the patent, whichever period is longer.

DETAILED DESCRIPTION OF THE INVENTION

Thermophilin 110 described in this invention and *S. thermophilus* strain 110 (NRRL B59671) can be used to kill certain bacteria that cause disease in humans and animals, and thus purified or concentrated thermophilin 110 and/or *S. thermophilus* strain 110 (NRRL B59671) may treat and/or prevent the diseases and/or reduce the symptoms associated with those diseases. Compositions containing thermophilin 110 and/or *S. thermophilus* strain 110 (NRRL B59671) may include, but are not limited to, lozenges, dissolvable strips, creams, ointments, lotions, mouthwashes, gum, gels, oil-in-water emulsions, water-in-oil, emulsions, tooth paste, cosmetics, and any other form appropriate for the application of the bacteria and/or thermophilin 110. It is understood that if one uses *S. thermophilus* strain 110 in a composition described herein, the bacteria produced and secreted thermophilin 110 prior to the generation of the composition and that thermophilin 110 and the bacteria are together combined with the other components of the composition.

Purified thermophilin 110 and/or *S. thermophilus* strain 110 (NRRL B59671) can be applied topically, orally, or parenterally to an animal to prevent the growth of or kill *S. pyogenes*, *S. mutans*, and/or *P. acnes* and thus prevent or treat diseases caused by the bacteria. Purified thermophilin 110 and/or *S. thermophilus* strain 110 (NRRL B59671) can also be used as a disinfectant, applied to surfaces to prevent the growth of and/or kill *S. pyogenes*, *S. mutans*, and/or *P. acnes*. It is understood that if one uses *S. thermophilus* strain 110 to prevent the growth of or kill these pathogens (and thus prevent or treat the diseases caused by these pathogens), *S. thermophilus* strain 110 produced and secreted thermophilin 110 prior to the generation of the composition and that thermophilin and the bacteria are together combined with the other components of the composition.

Because this invention involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or polyacrylamide gel electrophoresis, from sequenced nucleic acids, or from published DNA sequences. For proteins, sizes are given in kilodaltons (kDa or KDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)). Because of the degeneracy of nucleic acid codons, one can use various different polynucleotides to encode identical polypeptides. Table 1, infra, contains information about which nucleic acid codons encode which amino acids.

TABLE 1

| Amino acid | Nucleic acid codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere the least with the biological activity or actually enhances the biological activity of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 2 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 2

| Amino Acid | Conservative Substitute |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |
| Thr | Ser, Val |
| Trp | Phe, Tyr |
| Tyr | His, Phe, Trp |
| Val | Ile, Leu, Thr |

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native polyacrylamide gel electrophoresis or by anion-exchange HPLC as described in Pearson & Reanier, *J. Chrom.* 255: 137-149 (1983).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any change to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e, organism not subjected to the mutagens). Also, an organism that has been bred to incorporate a mutation into its genetic material is a genetically altered organism.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosome(s) or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

As discussed infra, the DNA sequence of mature BlpU is operably linked to the DNA sequence encoding glutathione S transferase (GST) in an expression vector and to a promoter. When this promoter is active, the expression vector causes the production of a fusion protein, also referred to a chimeric protein. The fusion protein contains the two or more different polypeptides or proteins linked together as a single protein. For the purposes of this invention, the fusion protein involves BlpU linked to a heterologous protein or polypeptide that may be useful for the production of BlpU and/or isolation of BlpU. Non-limiting examples of the heterologous proteins or polypeptides that can be linked to BlpU include 6× histidine, glutathione S transferase, myc, serum albumin, chitin binding protein, maltose binding protein, thioredoxin, and poly(NANP). BlpU can be linked to the heterologous protein or polypeptide at the amino terminus or carboxyl terminus of BlpU. The DNA encoding BlpU and the heterologous protein or polypeptide will need to be operably linked in the appropriate manner to generate the desired fusion protein. Linker amino acids can optionally exist between the two domains of the fusion protein. The goal of the producing a fusion protein is to enable one to isolate and purify BlpU by isolating and then processing the fusion protein such that BlpU is separated from the fusion protein. In one embodiment, separation of BlpU from the fusion protein occurs by cleaving the fusion protein with an enzyme (protease) that is selected to cut the fusion protein at specific amino acids (a recognition site) that is located between BlpU and the heterologous protein or polypeptide. Then BlpU can be purified or concentrated.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994—current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

An "active agent" is any composition containing thermophilin 110 and/or *S. thermophilus* strain 110 (NRRL B59671) alone or in combination with other compounds, which themselves may kill or prevent the growth of *S. pyogenes, S. mutans*, and/or *P. acnes*, and/or may prevent or treat a disease caused by *S. pyogenes, S. mutans*, and/or *P. acnes*, and/or may reduce the symptoms of such diseases.

A "therapeutically effective amount" or "effective amount" or "effective dose" of an active agent is a dose sufficient to either prevent and/or treat a disease in an animal (including a human) to which the active agent is administered or to prevent and/or treat a bacterial infection caused by *S. pyogenes, S. mutans*, and/or *P. acnes*, or other bacteria susceptible to the active agent of this invention in or on an animal, including human. The therapeutically effective amount of the active agent which can treat or prevent a bacterial infection can be determined by one of ordinary skill in the art by running routine trials with appropriate controls. Thermophilin 110 and/or *S. thermophilus* strain 110 (NRRL B59671) and/or compositions containing thermophilin 110 and/or *S. thermophilus* strain 110 (NRRL B59671) are administered in an amount effective to control the population(s) of the target bacteria in or on animals and surfaces of items. The effective amount will also significantly reduce or eliminate the population(s) of the target bacteria, and/or reduce the incidence of infection by these bacteria in and/or on a treated animal in comparison to untreated control animal. Comparison of the appropriate treatment groups to the controls will indicate whether a particular dosage of thermophilin 110 and/or *S. thermophilus* strain 110 (NRRL B59671) and/or compositions containing thermophilin 110 and/or *S. thermophilus* strain 110 (NRRL B59671) are effective in preventing or treating the bacterial infection, and thus is a therapeutically effective amount. It is understood in the art that the amount of the active agent administered or applied to the animal should be the amount that is effective to control *S. pyogenes*, *S. mutans*, and *P. acnes*. In addition, the type, size and condition of the animal being treated must be taken into consideration. For example, when controlling *S. pyogenes* which is responsible for strep throat, the therapeutically effective amount of the compounds of this invention will vary depending on the type and size of the human (e.g., infant, toddler, adolescent, adult) being treated. Yet, that therapeutically effective amount may differ from an effective dose to prevent infection from *P. acnes* or *S. mutans*. Also, when determining the effective dose, one should consider the age, body weight, general health, sex and diet of the animal, the time of administration, the route of administration, the rate of excretion of the compound or composition of this invention, the duration of the treatment, drugs or other compounds used in combination or coincidental with the administration of the compound or compositions of this invention, and other well known in the field. A therapeutically effective amount may be achieved by a single dose or multiple doses.

Treatment is the medical management of an animal, including human, with the intent to cure, ameliorate, stabilize, or prevent a disease, infection, pathological condition, or disorder. "Treatment" includes (i) active treatment, that is, treatment directed specifically toward the improvement of a disease, infection, pathological condition, or disorder; (ii) causal treatment, that is, treatment directed toward removal of the cause of the associated disease, infection, pathological condition, or disorder; (iii) palliative treatment, that is, treatment designed for the relief of symptoms rather than the curing of the disease, infection, pathological condition, or disorder; (iv) preventative treatment, that is, treatment directed to minimizing or partially or completely inhibiting the development of the associated disease, infection, pathological condition, or disorder; and (v) supportive treatment, that is, treatment employed to supplement another specific therapy directed toward the improvement of the associated disease, pathological condition, or disorder.

Exemplary administration of the active agents or compositions containing the active agents can be a relatively short-term period lasting approximately one or approximately two days, approximately one or approximately two weeks, or approximately one, approximately two or even approximately three months. Exemplary administration of the active agents or compositions containing the active agents can be a relatively long-term period lasting from approximately three or approximately four months to approximately one year, or even longer. In one embodiment, the suitable dosages of the active agents or compositions containing the active agents described herein can range from approximately 0.01 mg/kg/day to approximately 10 g/kg/day of the body weight of the animal to which the active agents or compositions containing the active agents are applied or administered. In another embodiment, the suitable dosages of the active agents or compositions containing the active agents described herein can range from approximately 0.1 mg/kg/day to approximately 1 g/kg/day of the body weight of the animal to which the active agents or compositions containing the active agents are applied or administered. In yet another embodiment, the suitable dosage can range from approximately 1 mg/kg/day to approximately 500 mg/kg/day of body weight.

The active agents or compositions containing the active agents of the present invention may be administered to or applied onto an animal directly. In another embodiment, the active agents or compositions containing the active agents may be mixed with an animal's feed or water. In yet another embodiment, the active agents or compositions containing the active agents may be further formulated with a carrier (pharmaceutically or veterinarianly acceptable carrier) to facilitate administration.

The carrier can take a wide variety of forms depending on the form of preparation desired for administration, e.g., oral or parenteral (including intravenous), or application, e.g., applied topically or on the surface. The active agents or compositions containing the active agents of the present invention can be presented as discrete units suitable for oral administration, such as capsules, cachets or tablets, lozenges, dissolvable strips, etc., each containing a predetermined amount of the active agents or compositions containing the active agents of this invention. Further, the active agents or compositions containing the active agents can be presented as a powder, as a cream, as an ointment, as granules, as a solution, as a suspension in an aqueous liquid, as a non-aqueous liquid, as an oil-in-water emulsion or as a water-in-oil liquid emulsion. In addition to the common dosage forms set out above, the active agents or compositions containing the active agents of the invention can also be administered by controlled release devices and/or delivery devices. The active agents or compositions containing the active agents can be prepared by any of the methods known to one of skill in the art. In general, such methods include a step of bringing into association the active agents or compositions containing the active agents with the carrier that constitutes one or more necessary ingredients. In general, the compositions are prepared by uniformly and intimately admixing the active agents or compositions containing the active agents with liquid carriers or finely divided solid carriers or both. The product can then be conveniently shaped into the desired presentation.

In preparing the active agents for oral dosage form, any convenient pharmaceutical or veterinarian carriers can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Optionally, tablets can be coated by standard aqueous or non-aqueous techniques. Non-limited examples of carriers include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, stearic acid, magnesium, and mineral oils. Suitable carriers and formulations are described in detail in *Remington's Pharmaceutical Sciences* (19th ed., 1995). In one embodiment, when referring to thermophilin 110, the carrier is not *S. thermophilus* strain 110. In other embodiments, when referring to thermophilin 110, it is understood from the context of the text that the carrier is not *S. thermophilus* strain 110.

The active agents of the present invention suitable for parenteral administration can be prepared as solutions or suspensions or emulsions or dispersions of the active agents in water or other liquid. A suitable surfactant can be included; such as, for example, hydroxypropylcellulose. The active agents can also be prepared in glycerol, liquid polyethylene glycols, and mixtures thereof in oils. Further, a preservative can be included to prevent the detrimental growth of microorganisms.

If applicable, a tablet containing the active agents of this invention can be prepared by compression or molding, optionally with one or more accessory ingredients or adjuvants. Compressed tablets can be prepared by compressing, in a suitable machine, the active agents of the invention in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing the compound(s) of the invention via conventional processing methods. As an example, a cream or ointment is prepared by mixing hydrophilic material and water, together with about 5 wt % to about 10 wt % of the active agent(s) to produce a cream or ointment having a desired consistency.

As a disinfectant, the active agent(s) can be made into a solution, suspension, gel, or spray that can be wiped on, sprayed on, poured on, etc., onto a surface. It also can be a solution, suspension, or gel into which a body part or object is dipped. It can also be made into a solution, suspension, gel, or similar type of compound that can be applied to an object or animal or part of an animal. Such disinfecting solutions, suspensions, gels, or sprays containing one or more the active agent(s) can be applied to medical or veterinarian instruments, especially those for which are sensitive to extreme heat and/or pressure and thus would be damaged by autoclaving. In such disinfectant solutions, suspensions, gels, or sprays, the amount of each active agent can range between approximately 0.001 µg/ml to approximately 1 g/ml in one embodiment, between approximately 0.01 µg/ml to approximately 100 mg/ml in another embodiment, between approximately 0.1 µg/ml to approximately 10 mg/ml in another embodiment, or between approximately 1 µg/ml to approximately 1 mg/ml in another embodiment.

One type of disinfectant solution or suspension can be a mouthwash. Such a mouthwash may have one or more of the following ingredients water, phenol, thymol, eugenol, eucalyptol, menthol, alcohol, chlorhexidine gluconate, cetylpyridinium chloride, hexetidine, benzoic acid, methyl salicylate, triclosan, benzalkonium chloride, methylparaben, hydrogen peroxide, domiphen bromide and/or fluoride. Some mouthwashes also include sweeteners, such as sorbitol, sucralose, sodium saccharin, and xylitol. The amount of the active agent can range from between approximately 0.001 µg/ml to approximately 1 g/ml in one embodiment, between approximately 0.01 µg/ml to approximately 100 mg/ml in another embodiment, between approximately 0.1 µg/ml to approximately 10 mg/ml in another embodiment, or between approximately 1 µg/ml to approximately 1 mg/ml in another embodiment.

In addition to the aforementioned carrier ingredients, the formulations described above can include, as appropriate, one or more additional carrier ingredients such as diluents, buffers, flavoring agents, binders, surface-active agents, thickeners, lubricants, preservatives (including anti-oxidants) and the like. Furthermore, compounds can be included to render the formulation isotonic with the blood of the intended recipient. Compositions containing the compound(s) of the invention can also be prepared in powder or liquid concentrate form.

In one aspect, the active agent(s) and compositions of this invention can be co-administered or co-applied with one or more other therapeutic agents, including other anti-microbial agents and/or pharmaceutically active or veterinarianly active agents, such as, but not limited to, geldanamycin, herbimycin, carbacephem, loracarbef, ertapenem, doripenem, imipenem/cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, macrolides, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, bacitracin, colistin, polymyxin B, quinolones, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanilimide, sulfasalazine, sulfisoxazole, trimethoprim, trimethoprim-sulfamethoxazole (TMP-SMX), demeclocycline, doxycycline, minocycline, oxytetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin or rifampicin, and/or tinidazole.

The active agent(s) and/or compositions of the present invention may be used either alone or in combination with an immunoregulatory agent ("adjuvant"). An adjuvant is a compound or mixture that enhances the animal's immune response.

In various aspects, an appropriate dosage level will generally be approximately 0.01 mg per kg body weight of the animal to approximately 10 g per kg body weight of the animal per day and can be administered in single or multiple doses. In one embodiment, the dosage level can be approximately 0.1 mg/kg/day to approximately 1 g/kg/day; in another embodiment approximately 0.5 mg/kg/day to approximately 500 mg/kg/day. In another embodiment, a suitable dosage level can be approximately 0.01 mg/kg/day to approximately 250 mg/kg/day; or alternatively approximately 0.05 mg/kg/day to approximately 100 mg/kg/day; or alternatively approximately 0.1 mg/kg/day to approximately 50 mg/kg/day. In other embodiments, the dosage can be approximately 0.05 mg/kg/day to approximately 0.5 mg/kg/day; approximately 0.5 mg/kg/day to approximately 5.0 mg/kg/day; or approximately 5.0 mg/kg/day to approximately 50 mg/kg/day. For oral administration, the compounds and compositions can be administered in the form of tablets containing approximately 1.0 mg to 1000 mg of the active agent, or alternatively, approximately 1.0 mg, approximately 5.0 mg, approximately 10 mg, approximately 15 mg, approximately 20 mg, approximately 25 mg, approximately 50 mg, approximately 75 mg, approximately 100 mg, approximately 150 mg, approximately 200 mg, approximately 250 mg, approximately 300 mg, approximately 400 mg, approximately 500 mg, approximately 600 mg, approximately 750 mg, approximately 800 mg, approximately 900 mg, or approximately 1000 mg of the active agent. The compound can be administered on a regimen of approximately 1 to approximately 4 times per day, or alternatively approximately once or approximately twice per day. This dosing regimen can be adjusted to provide the optimal therapeutic response.

The terms "approximately" and "about" refers to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

This invention described herein may be administered to bovine, swine, equine, ovine, goats, camels, and any other mammal including humans, birds (including but not limited to chickens, turkeys, quail, ducks, and other domesticated birds), amphibians, reptiles and fish.

Having described the invention in general, below are examples illustrating the generation and efficacy of the invention.

Example 1

Characterization of the S. thermophilus Strain 110 (NRRL B59671) Blp Gene Cluster Streptococcus thermophilus strain 110 (NRRL B59671) and S. thermophilus strain LMD-9 are both capable of producing a bacteriocin with broad spectrum antimicrobial activity (Gilbreth & Somkuti (2005); Fontaine & Hols (2008)). Production of both bacteriocins has been shown to require a functional quorum sensing system which is encoded within a cluster of genes that have been fully characterized in S. thermophilus strain LMD-9 (Fontaine, et al. (2007); Renye & Somkuti (2013)). However, the two bacteria differ in that bacteriocin production in S. thermophilus strain 110 (NRRL B58671) occurs naturally in batch culture, whereas in S. thermophilus strain LMD-9, bacteriocin production must be activated by overexpression of blpC or supplementation of the growth medium with excess QSIP. To better understand why production occurs naturally in S. thermophilus strain 110 (NRRL B58671), the entire gene cluster is sequenced. In Example 3, infra, the transcription of blp components are measured and compared with their counterparts in S. thermophilus strain LMD-9.

Figure 1:
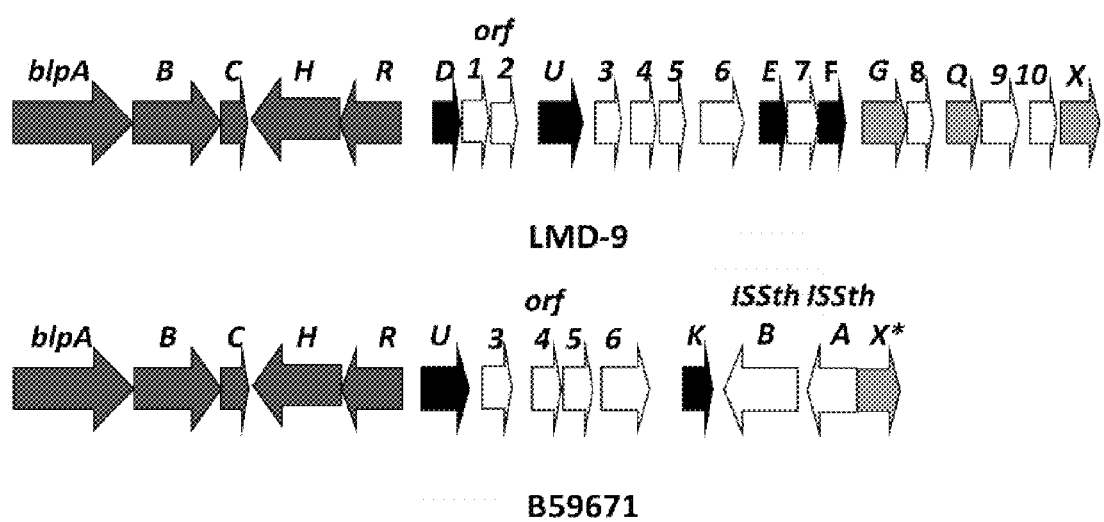
FIG. 1 compares the map of the bacteriocin-like peptide (blp) gene cluster in *S. thermophilus* strain LMD-9 and *S. thermophilus* strain 110 (NRRL B59671). Characterized blp genes are designated by letters and grouped by color: components of the quorum sensing system (dark gray); potential bacteriocins with a double-glycine leader sequence (black); and accessory proteins (light gray). Additional open reading frames (ORFs) are designated by numbers and white arrows. *S. thermophilus* strain 110 (NRRL B59671) contains two insertion elements (ISSthA and ISSthB), and has a truncated blpX (*).

Chromosome walking is performed on S. thermophilus strain 110 (NRRL B59671) to determine the components of its blp locus. Initial primers are designed to the 5' end of blpA (SEQ ID NO: 3) and the 3' end of blpX (SEQ ID NO: 4) which are reported to flank the blp gene cluster in S. thermophilus strains LMD-9, LMG18311 and CNRZ1066 (Hols, et al. (2005)) (see FIG. 1). After each round of sequencing, a new 5'-primer and 3'-primer are designed based on the obtained sequence. Chromosome walking is continued until the entire gene cluster is sequenced in both directions, allowing for a single contig to be constructed. Nucleic acid sequencing is performed using an ABI PRISM 3730 DNA analyzer (Perkin-Elmer, Waltham, Mass.) with ABI PRISM Big Dye terminator cycle sequencing reagent (Perkin-Elmer, Waltham, Mass.). Sequences are analyzed, and contigs are created using Sequencher 4.9 (Gene Codes Corp, Ann Arbor, Mich.). A subsequent search for open reading frames (ORFs) identifies 14 potential genes (see FIG. 1). ORF identification and promoter analysis are performed using Clone Manager software (Sci-ed Software, Cary, N.C.). Prediction of CovR binding site is done using the Virtual Footprint Promoter Analysis tool from the prokaryotic database of gene regulation (Prodoric) (Munch, et al., Nucleic Acids Res 31, 266-269 (2003)). Analysis of the ORFs identifies a three gene operon at one end of the gene cluster that contained homologs of blpA, blpB and blpC which shared 99, 99 and 100% identity with the corresponding genes in S. thermophilus strain LMD-9 (GenBank Accession number: CP000419), S. thermophilus strain ND03 (GenBank Accession number: CP002340), S. thermophilus strain JIM8232 (GenBank Accession number: FR875178) and S. thermophilus strain MN-ZLW002 (GenBank Accession number: CP003499) respectively. Further analysis of the predicted proteins show a 99% identity to BlpA and BlpB from S. thermophilus strain LMD-9, confirming that BlpB is not truncated as previously described for S. thermophilus strain CNRZ1066 and S. thermophilus strain LMG18311 (Hols, et al. (2005)). The predicted 53 amino acid prepeptide encoded by blpC shows 100% identity to the prepeptide expressed in S. thermophilus strain LMD-9 (Fontaine, et al. (2007)). Immediately downstream of the blpABC operon is a two gene operon encoded on the opposite strand of the chromosome. This operon contains homologs of blpR and blpH which show 99% identity to the respective genes in S. thermophilus strain ND03, S. thermophilus strain LMG18311, and S. thermophilus strain CNRZ1066. When compared to S. thermophilus strain LMD-9, the nucleotide identity for both genes are slightly less at 98%, and the predicted proteins have 97% identity, with BlpR and BlpH having 7 and 11 amino acid substitutions respectively. The presence of these two operons and their genetic orientation are confirmed in all sequenced strains of S. thermophilus which possess the blp gene cluster (Bolotin, et al., Nat. Biotechnol. 22, 1554-8 (2004); Fontaine, et al. (2007); Sun, et al., J. Bacteriol. 193, 793-4 (2011); Kang, et al., J. Bacteriol. 194, 4428-9 (2012)).

The region downstream of the blpRH operon in S. thermophilus strain 110 (NRRL B59671) contains two ORFs which encode putative antimicrobial peptides based on the presence of a double glycine (GG) leader sequence. BLAST analysis of the first ORF show 100% identity with blpU from S. thermophilus strain LMD-9 and S. thermophilus strain LMG18311 (GenBank Accession number: CP000023), and is part of a two gene operon with a homolog of orf3 (99% identity with S. thermophilus strain LMD-9, S. thermophilus strain LMG18311, *S. thermophilus* strain ND03, *S. thermophilus* strain MN-ZLW-002 and *S. thermophilus* strain JIM8232). This two gene operon is followed by 3 ORFs homologous to orf4, 5 and 6 in *S. thermophilus* strain LMD-9 (Fontaine & Hols (2008)), and an ORF with 99% identity to blpK in *S. thermophilus* strain CNRZ1066 and *S. thermophilus* strain LMG18311. In *S. thermophilus* strain LMG18311, a one base pair deletion near the 5' end of the gene shifts the coding sequence out of frame resulting in a truncated peptide of 46 amino acids, compared to the predicted 81 amino acid peptide encoded by blpK in *S. thermophilus* strain 110 (NRRL B59671) and *S. thermophilus* strain CNRZ1066. In *S. thermophilus* strain LMD-9, bacteriocin activity is dependent on the presence of blpD (Fontaine & Hols (2008)), but blpD's absence in the *S. thermophilus* strain 110 (NRRL B59671) gene cluster suggests that blpU or blpK encode the actual bacteriocin.

Positioned downstream of blpK, encoded in the opposite orientation, are homologs to orfA and orfB of the ISSth1 transposase. The location of the inserted transposase in *S. thermophilus* strain 110 (NRRL B59671) is identical to what was reported for *S. thermophilus* strain CNRZ1066, where the 5' end of orfA overlaps the 5' end of blpX, resulting in a truncated copy of both genes (Hols, et al. (2005)). The orfA and orfB components of ISSth1 are also identified in *S. thermophilus* strain LMG18311, *S. thermophilus* strain MN-ZLW-002, *S. thermophilus* strain ND03, and *S. thermophilus* strain JIM8232; however orfA remains intact in these strains and the transposase is located upstream of blpG. This configuration allows the later strains to maintain intact homologs of blpG, blpQ and blpX. Of the strains that have been sequenced, or in which the blp locus has been partially characterized, only *S. thermophilus* strain LMD-9 and *S. thermophilus* strain PR136 are reported to contain the three gene operon of blpE/orf7/blpF, without the presence of the ISSth1 transposase.

The nucleic acid sequence upstream of blpABC, blpRH, blpU-orf3 and blpK in *S. thermophilus* strain 110 (NRRL B59671) are compared with *S. thermophilus* strain LMD-9 to determine differences that may exist within promoter regions of these operons or genes. Sequence analysis confirms that the blpABC promoter in *S. thermophilus* strain 110 (NRRL B59671) is identical to the characterized region describe for *S. thermophilus* strain LMD-9. This includes the two imperfect direct repeats, LR: ACCGTTTGGGACG (SEQ ID NO: 5) and DR: ACTTTTTGGGACG (SEQ ID NO: 6), which are essential for QSIP induced gene expression (Blomqvist, et al. (2006)). Sequence analysis of the promoter region upstream of blpU-orf3 and blpK are identical, and match the characterized promoter region described for the blpE/orf7/blpF operon in *S. thermophilus* strain LMD-9. Thus, the blpU promoter for *S. thermophilus* strain 110 (NRRL B59671) differs from the blpU promoter in *S. thermophilus* strain LMD-9 by two nucleotides in the LR sequence: ACC<u>AT</u>TCGGGACA (*S. thermophilus* strain 110 (B59671); SEQ ID NO: 7) and ACT<u>AC</u>TCGGGACA (*S. thermophilus* strain LMD-9; SEQ ID NO: 8) (Fontaine, et al. (2007)). The blpRH promoter region defined by Fontaine, et al. (2007) for *S. thermophilus* strain LMD-9 also differs from the sequence obtained for *S. thermophilus* strain 110 (NRRL B59671). An additional four adenines are present in the *S. thermophilus* strain 110(NRRL B59671) promoter resulting in a run of 12 adenines at the 5' end of this region, and a nucleotide substitution (adenine to guanine) located 37 bases upstream of the blpR start codon results in the presence of recognition sequence (CAATTTTTC<u>A</u>ATAAAC) (SEQ ID NO: 9) for CovR, a streptococcal global response regulator (Lamy, et al., *Mol. Microbiol.* 54, 1250-68 (2004)). Not wishing to be bound to any hypothesis, this substitution allows for the formation of a more stable hairpin structure with a free energy of –2.7, as compared to a free energy of –1.7 in *S. thermophilus* strain LMD-9.

Example 2

Comparison of Bacteriocin Activity in *S. thermophilus* Strain 110 (NRRL B59671) and *S. thermophilus* Strain LMD-9

Bacteriocin activity is measured using an agar diffusion method (see, Gilbreth & Somkuti (2005)). Cultures of *S. thermophilus* strain 110 (NRRL B59671) and *S. thermophilus* strain LMD-9 are grown at 37° C. to an $OD_{660}$ between 0.8 and 1.0 in 10 ml tryptone-yeast extract medium (Somkuti & Steinberg 1986) formulated with lactose (TYL) or glucose (TYG), or M17 medium (Becton Dickinson Co., Sparks, Md.) formulated with glucose (M17G) or lactose (M17L). Cells are pelleted by high-speed centrifugation for collection of cell-free supernatants (CFS). CFS (~50 μl) are loaded into precast wells in an agar medium seeded with the target bacteria (0.5% v/v). Bacterial targets included: *S. thermophilus* strain ST113 in TYL, *P. acidilactici* in MRS (Becton Dickinson Co., Sparks, Md.), and *L. innocua* in BHI (Beckton Dickinson Co., Sparks, Md.). Plates are allowed to equilibrate overnight at 4° C., and then are incubated at 37° C. for 8 hours and are examined for the appearance of zones of inhibition.

Previously it was shown that *S. thermophilus* strain 110 (NRRL B59671) naturally produces a bacteriocin with anti-pediococcal activity when grown in TYL medium (Gilbreth & Somkuti (2005)), and that this activity was lost when blpC was deleted from the chromosome (Renye & Somkuti (2013)). When *S. thermophilus* strain LMD-9 is grown in the same medium supplemented with QSIP at concentrations ranging from 250 to 1000 ng/ml, anti-microbial activity against *S. thermophilus* strain ST113 is not detected (see top, middle well in FIG. 2)

Figure 2:
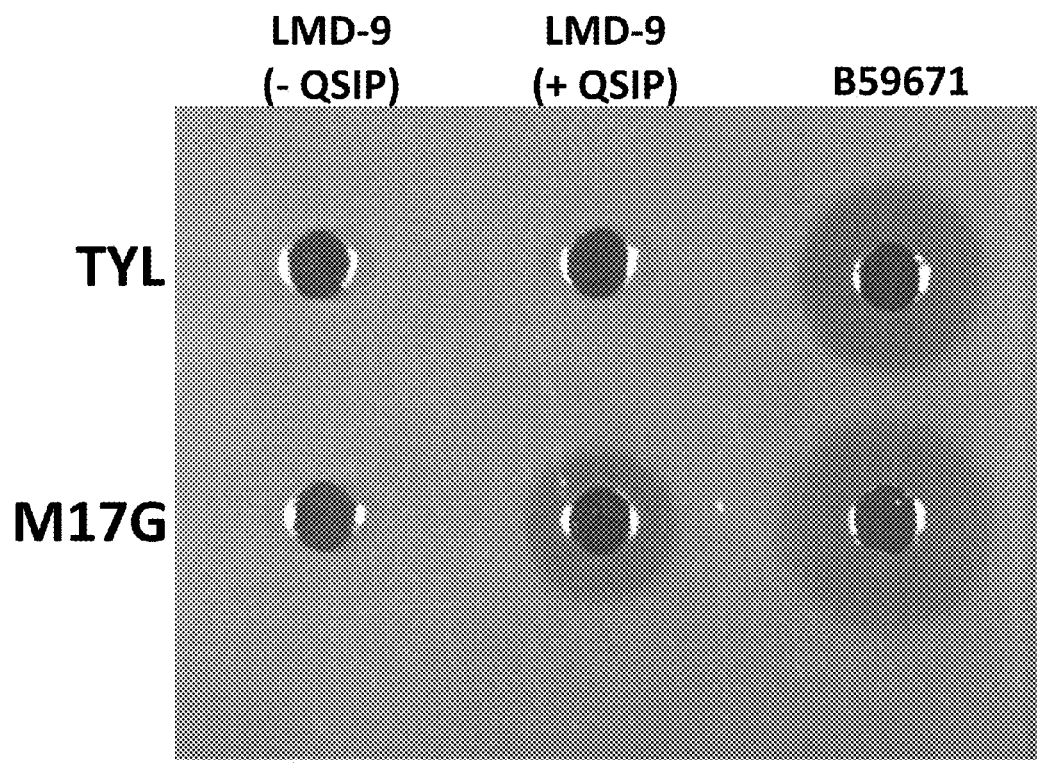
FIG. 2 is a photograph of a plate of typtone-yeast extract medium with lactose (TYL) seeded with a lawn of *S. thermophilus* strain ST113 and having six wells in the agar. Cell-free supernants (CFS) from *S. thermophilus* strain LMD-9 grown in the presence (+QSIP) or absence (−QSIP) of 250 ng ml$^{-1}$ of the 30-mer quorum sensing induction peptide (QSIP) and grown in either TYL (top half of plate) or in M17G (bottom half of plate) medium are placed in the four indicated wells. CFS from *S. thermophilus* strain 110 (NRRL B59671) grown in either TYL (top half of plate) or in M17G (bottom half of plate) medium are placed in the two indicated wells. The clear zones surrounding the wells containing CFS from *S. thermophilus* strain 110 (NRRL B59671) and from *S. thermophilus* strain LMD-9 grown in the presence (+QSIP) in M17G medium indicate bacteriocin activity.

When carried out in M17G, the addition of 250 ng/ml of QSIP induces bacteriocin production in *S. thermophilus* strain LMD-9 which inhibits the growth of *S. thermophilus* strain ST113 (see bottom, middle well FIG. 2), but, contrary to previously published reports, LMD-9 fails to inhibit the growth of *L. innocua* (data not shown). *S. thermophilus* strain 110 (NRRL B59671) naturally produces thermophilin 110 in M17G and TYL and inhibits the growth of both *P. acidilactici* (data not shown) and *S. thermophilus* strain ST113 (see right top and bottom wells in FIG. 2). CFS of *S. thermophilus* strain 110 (NRRL B59671) also displays mild inhibition of *L. innocua* (data not shown). Supplementation of M17 medium with lactose (M17L) or TY base medium with glucose (TYG) does not affect bacteriocin production by *S. thermophilus* strain 110 (NRRL B59671) (data not shown), confirming that the sugar content of the medium is not responsible for the differences observed.

Example 3

Expression of Blp Components in *S. thermophilus* Strain 110 (NRRL B59671) and *S. Thermophilus* Strain LMD-9

Real-time PCR analysis is used to measure the transcription of blp components in *S. thermophilus* strain 110 (NRRL B59671) and *S. thermophilus* strain LMD-9 grown in both TYL and M17G (10 ml) until late exponential phase ($OD_{660}$ between 0.8 and 1.0). mRNA levels in *S. thermophilus* strain 110 (NRRL B59671) and QSIP-induced *S. thermophilus* strain LMD-9 are measured semi-quantitatively and are expressed as a fold-increase when compared to non-induced mRNA levels in *S. thermophilus* strain LMD-9. Cell lysis and RNA extraction is carried out using the RiboPure™-Bacteria kit (Life Technologies, Carlsbad, Calif.) according to manufacturer's protocol. To eliminate any residual DNA, RNA is treated with 8 units of DNase I (Life Technologies, Carlsbad, Calif.) for 30 minutes at 37° C. RT-PCR is performed on isolated RNA using an Applied Biosystems 7500 Fast RT-PCR system (Life Technologies, Carlsbad, Calif.). Forward and reverse primers for blpC and 16S rRNA (reference gene) are provided in Table 3 infra. Cycling conditions are: 40 cycles of 95° C. for 30 seconds, 45° C. for 30 seconds and 60° C. for 30 seconds. A melt curve analysis is performed from 60-95° C. with fluorescence readings taken continuously after a 1% increase in temperature. cDNA synthesis and RT-PCR are carried out in a single step using the SuperScript III Platinum SYBR Green One-Step qRT-PCR kit (Life Technologies, Carlsbad, Calif.) with a total RNA concentration of 1 μg for amplification of targeted blp components, and 10 ng for 16 S rRNA. The ABI 7500 Fast software is used to determined $C_T$ values, and the relative quantification of gene expression is determined using the $2^{-\Delta\Delta C_T}$ method (Livak & Schmittgen, *Methods* 25, 402-8 (2001)), where $\Delta C_T = C_T$ (target)$-C_T$ (reference), and $\Delta\Delta C_T = C_T$ (test culture)$-C_T$ (control culture). Results are reported from a minimum of three independent RT-PCR reactions.

Figure 3:
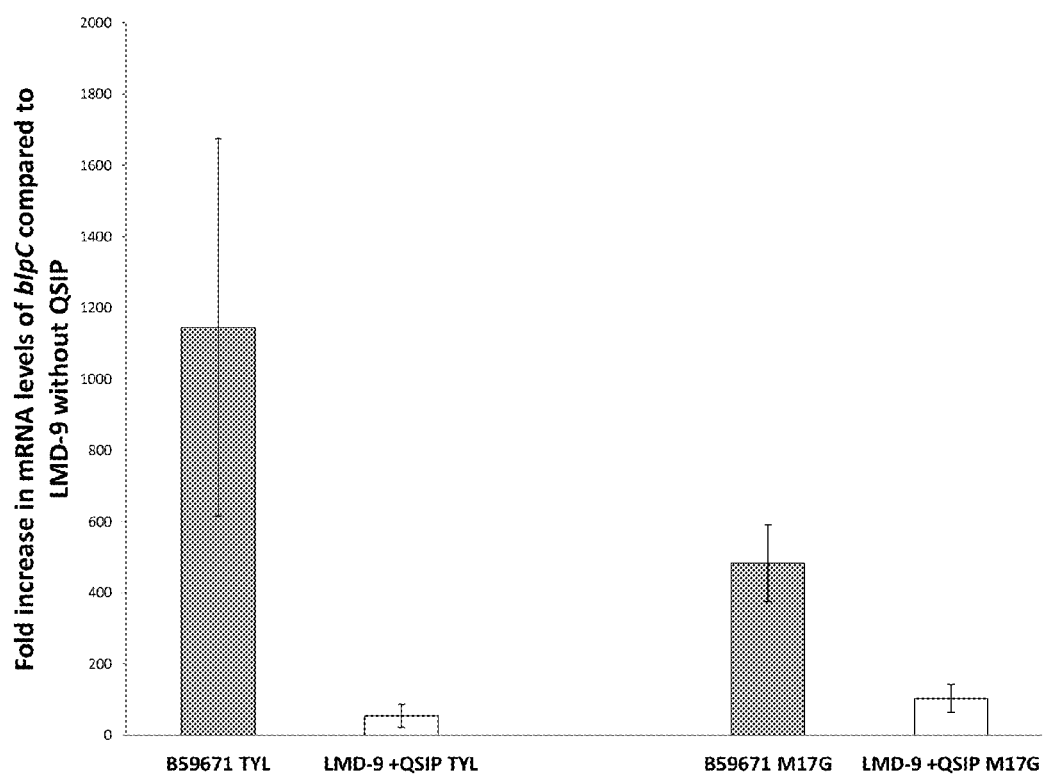
FIG. 3 shows the fold-increase of blpC mRNA expression as determined by real-time PCR analysis in *S. thermophilus* strain 110 (NRRL B59671) (gray bars) and *S. thermophilus* strain LMD-9 with QSIP (white bars) in tryptone yeast extract (TYL) or in M17 glucose (M17G) medium. mRNA expression of blpC in non-induced *S. thermophilus* strain LMD-9 culture without QSIP in TYL or M17G is used as the base line level. Data are the average of at least three independent experiments (±standard deviation).

The level of blpC mRNA is representative of the expression of the blpABC operon which is regulated by a QSIP-inducible promoter. Expression of blpC is substantially higher in *S. thermophilus* strain 110 (NRRL B59671) when compared to both non-induced and induced cultures of *S. thermophilus* strain LMD-9. In *S. thermophilus* strain 110 (NRRL B59671), the expression of blpC is determined to be an average of 1145- and 488-fold higher than what is observed in a non-induced culture of *S. thermophilus* strain LMD-9 grown in TYL and M17G respectively (see FIG. 3). The addition of 250 ng/ml QSIP increases expression of blpC in *S. thermophilus* strain LMD-9 by an average of 54-fold (TYL) and 103-fold (M171G), but is still approximately 21-fold and 5-fold lower than what is observed naturally in *S. thermophilus* strain 110 (NRRL B59671) grown in TYL and M17G respectively (see FIG. 3).

The only potential bacteriocin-encoding gene common to both *S. thermophilus* strain 110 (NRRL B59671) and *S. thermophilus* strain LMD-9 is blpU, thus its expression is tested. *S. thermophilus* strain 110 (NRRL B59671) and *S. thermophilus* strain LMD-9 are grown in both TYL and M17G (10 ml) until late exponential phase ($OD_{660}$ between 0.8 and 1.0). Expression of blpD in *S. thermophilus* strain LMD-9 is also measured because it was reported to encode the actual bacteriocin in *S. thermophilus* strain LMD-9 (Fontaine & Hols (2008)). Because a homolog of blpD does not exist in *S. thermophilus* strain 110 (NRRL B59671), the expression of blpK, which potentially encodes for an antimicrobial peptide, is measured. Expression of blpU and blpK in *S. thermophilus* strain 110 (NRRL B59671) and blpU and blpD in QSIP-induced *S. thermophilus* strain LMD-9 are measured semi-quantitatively and are expressed as a fold-increase when compared to non-induced expression levels in *S. thermophilus* strain LMD-9. Total RNA are isolated from the bacteria as described above using RiboPure™-Bacteria kit (Life Technologies, Carlsbad, Calif.). To eliminate any residual DNA, RNA is treated with 8 units of DNase I (Life Technologies, Carlsbad, Calif.) for 30 minutes at 37° C. RT-PCR is performed on isolated RNA using an Applied Biosystems 7500 Fast RT-PCR system (Life Technologies, Carlsbad, Calif.). Forward and revers primers for blpD, blpK, blpU, and 16s rRNA (reference gene) are provided in Table 3 infra. Cycling conditions are: 40 cycles of 95° C. for 30 seconds, 45° C. for 30 seconds and 60° C. for 30 seconds. A melt curve analysis is performed from 60-95° C. with fluorescence readings taken continuously after a 1% increase in temperature. cDNA synthesis and RT-PCR are carried out in a single step using the SuperScript III Platinum SYBR Green One-Step qRT-PCR kit (Life Technologies, Carlsbad, Calif.) with a total RNA concentration of 1 μg for amplification of blpU and blpD each, and 10 ng for 16 S rRNA gene. The ABI 7500 Fast software is used to determined $C_T$ values, and the relative quantification of gene expression is determined using the $2^{-\Delta\Delta C_T}$ method (Livak & Schmittgen, *Methods* 25, 402-8 (2001)), where $\Delta C_T = C_T$ (target)$-C_T$ (reference), and $ME_T = C_T$ (test culture)$-C_T$ (control culture). Results are reported from a minimum of three independent RT-PCR reactions.

Figure 4:
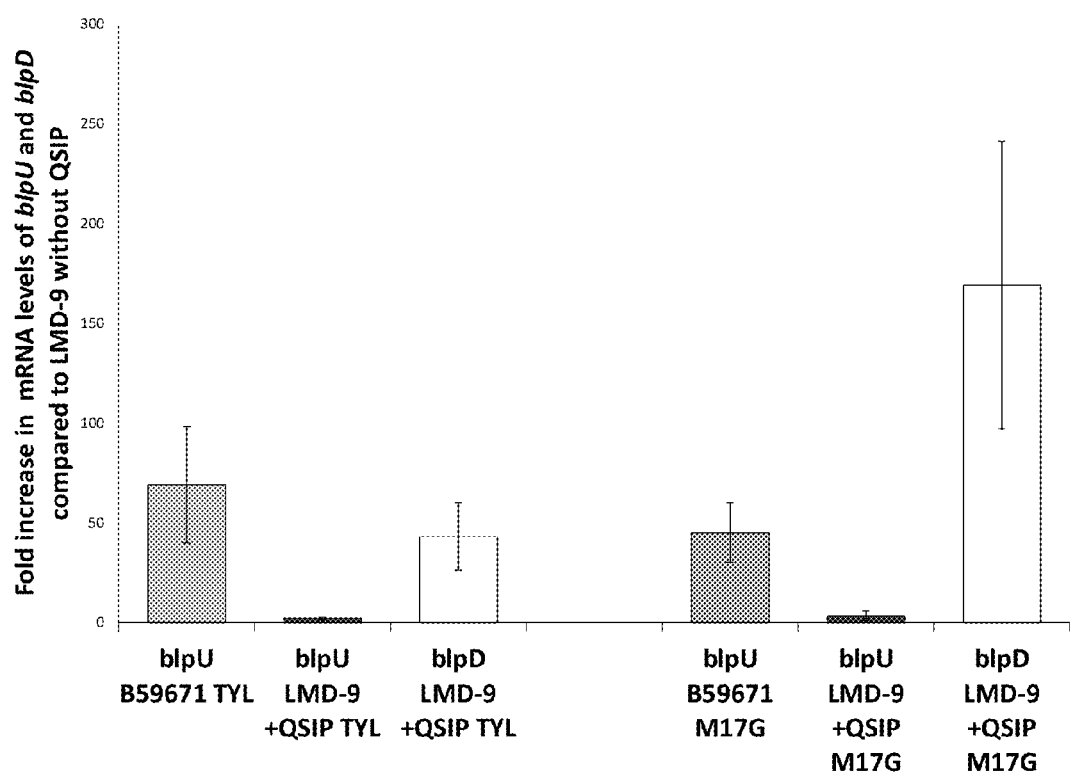
FIG. 4 shows the fold-increase of mRNA expression, as determined by RT-PCR, of blpU in *S. thermophilus* strain 110 (NRRL B59671) (light gray bars), and blpU (dark gray) and blpD (white) expression in *S. thermophilus* strain LMD-9 with QSIP. mRNA expression is measured in bacteria grown in both TYL and M17G media. mRNA expression of blpU and blpD in a non-induced *S. thermophilus* strain LMD-9 culture (no QSIP) is used as the base line level. Data are the average of at least three independent experiments (±standard deviation).

When grown in TYL and M17G media, the expression of blpU is significantly higher in *S. thermophilus* strain 110 (NRRL B59671) as compared to both non-induced and QSIP-induced cultures of *S. thermophilus* strain LMD-9 (see FIG. 4). When compared to a non-induced *S. thermophilus* strain LMD-9 culture, the expression of blpU is 69-fold and 45-fold higher in *S. thermophilus* strain 110 (NRRL B59671) grown in TYL and M17G respectively. QSIP induction of *S. thermophilus* strain LMD-9 only results in a 2-fold (TYL) or 3-fold (M17G) increase in blpU expression. Expression of blpD is increased by 43-fold in TYL and 169-fold in M17G after QSIP induction (see FIG. 4). Expression of blpK in *S. thermophilus* strain 110 (NRRL B59671) cannot be related to *S. thermophilus* strain LMD-9 because a homolog is not present, thus blpK expression is measured in comparison with blpU expression from *S. thermophilus* strain 110 (NRRL B59671). The expression of blpU is an average of 3.5 (±0.07)-fold and 5.3 (±1.1)-fold higher than blpK when *S. thermophilus* strain 110 (NRRL B59671) is grown in TYL or M17G, respectively (data not shown).

Figure 5:
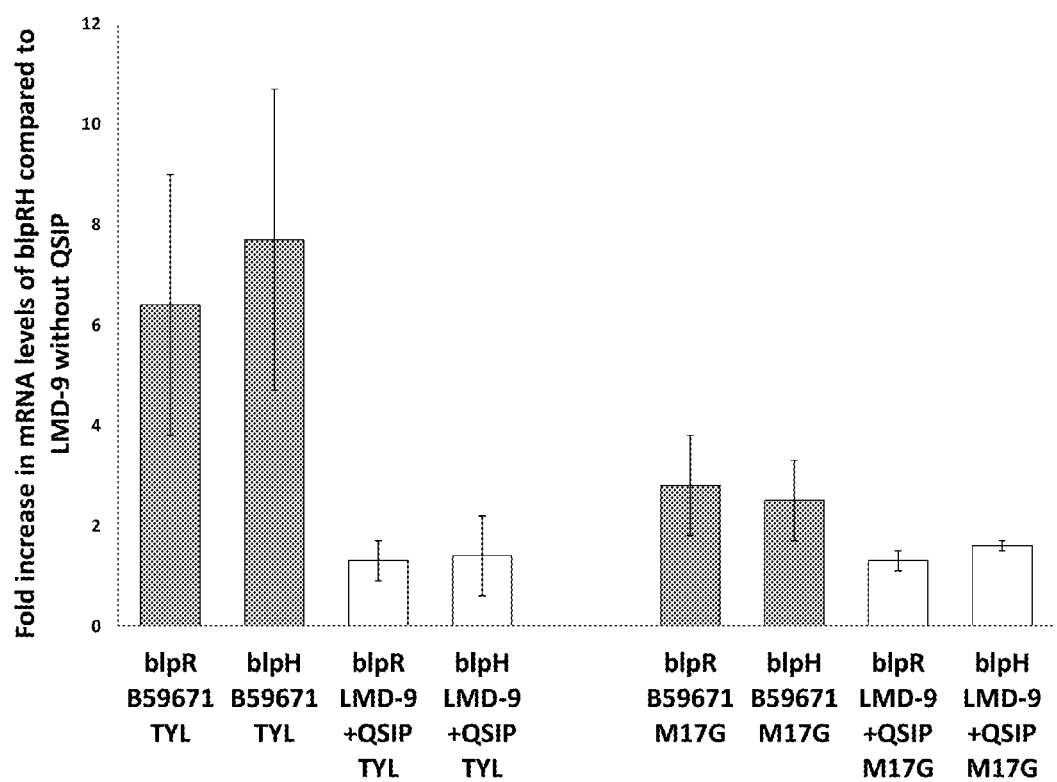
FIG. 5 shows the fold-increase of mRNA expression, as determined by RT-PCR, of blpR and blpH expression in *S. thermophilus* strain 110 (NRRL B59671) (gray bars) and *S. thermophilus* strain LMD-9 plus QSIP (white). mRNA expression is measured in both TYL and M17G media.

Because bacteriocin production in both *S. thermophilus* strain 110 (NRRL B59671) and *S. thermophilus* strain LMD-9 are regulated by the 30-mer QSIP, mRNA of the two component system (blpRH operon) required for responding to this signal are monitored by RT-PCR (using the protocol described supra), using the forward and reverse primers listed in Table 3 infra. Following QSIP-induction of *S. thermophilus* strain LMD-9, expression of the blpRH operon increases by approximately 1.5-fold in both TYL and M17G (see FIG. 5). For *S. thermophilus* strain 110 (NRRL-B59671), expression of the blpRH operon differs depending on the growth medium. In M17G, expression of the operon is approximately 2.5-fold higher than what is observed for a non-induced culture of *S. thermophilus* strain LMD-9. However, in TYL, blpRH expression is 7-fold higher when compared to a non-induced *S. thermophilus* strain LMD-9 culture (see FIG. 5).

TABLE 3

| Primer Name | Primer Sequence |
|---|---|
| 16S rRNA forward | CCTACGGGAGGCAGCAG (SEQ ID NO: 10) |
| 16S rRNA reverse | ATTACCGCGGCTGCTGG (SEQ ID NO: 11) |
| blpC forward | GGCTAACAATACGATTAA (SEQ ID NO: 12) |
| blpC reverse | GCTTGAGGAATGTTATAG (SEQ ID NO: 13) |
| blpU forward | CCACCAGCATGTTGCTCC (SEQ ID NO: 14) |
| blpU reverse | GCTAAACAAGGAGTAGCTAC (SEQ ID NO: 15) |
| blpK forward | CCTGCACCACCTAGAACACC (SEQ ID NO: 16) |
| blpK reverse | CACCCTTGACCTCGAAACAC (SEQ ID NO: 17) |
| blpD forward | GAAACAGTATAAGGCTGC (SEQ ID NO: 18) |
| blpD reverse | GGTTGTCCTGTGATGAGG (SEQ ID NO: 19) |
| blpR forward | AAACACCATGTTCACCTCCAG (SEQ ID NO: 20) |
| blpR reverse | CCGATGGCATGGGTAGAG (SEQ ID NO: 21) |
| blpH forward | TCGTGAAATGATTCAAGGACA (SEQ ID NO: 22) |
| blpH reverse | TCGTGTCTAAAACTACGAACAGAA (SEQ ID NO: 23) |

Example 4

Identification of Thermophilin 110

Primers are designed to amplify DNA fragments (~600 nucleotides) of the genes which flank blpK in the *S. thermophilus* strain 110 chromosome: orf6 (forward primer: CCCACTAGTCGCTAAGGGCTTACTTGA (SEQ ID NO: 24) and reverse primer: CCCCTGCAGGGAAATCTTCCTCTAATT (SEQ ID NO: 25)) and ISB (forward primer: CCCCTCGAGGCTTTGTTAGGTAATATC (SEQ ID NO: 26) and reverse primer: CCCGGTACCGAGGACAACATTCTCAATCG (SEQ ID NO: 27)). A linear DNA molecule is generated with the orf6 and ISB fragments flanking a kanamycin resistance gene. The linear DNA molecule (~2500 nucleotides) is inserted within *S. thermophilus* strain 110 (NRRL-B59671) using a standard electrotransformation protocol (Somkuti & Steinberg, 1988). Via a homologous recombination event with the DNA fragments flanking the kanamycin resistance gene, the blpK gene is deleted from the bacterial chromosome. Bacteria containing the insertion sequence are identified by their ability to grow in the presence of kanamycin, and further confirmed by PCR analysis. Antimicrobial activity of the mutant *S. thermophilus* strain 110 (NRLL-B59671) (blpK knock-out) is tested by the agar diffusion assay using the protocol described in Example 2 supra and using *P. acidilactici, S. thermophilus, S. pyogenes*, and *S. mutans* as target bacteria. Antimicrobial activity is the same for the *S. thermophilus* strain 110 (NRRL-B59671) and the blpK knock-out strain, demonstrating that blpK does not encode the thermophilin 110 peptide. Because blpK is considered one of two possible genes encoding an antimicrobial peptides and knocking out blpK does not destroy thermophilin activity in *S. thermophilus* strain 110 (NRRL-B59671), it is concluded that blpK does not encode the thermophilin peptide. This data indicates that blpU encodes the thermophilin peptide, as it is the only remaining gene within the blp cluster which encodes for a peptide with characteristics common to other bacteriocins.

Primers are designed to amplify DNA fragments (1000 nucleotides) containing the genes which flank blpU in the *S. thermophilus* strain 110 chromosome: blpHR (forward primer: CCCGGTACCGGAAAAAATACCTCAGAC (KpnI—restriction endonuclease recognition sequence underlined) (SEQ ID NO: 28) and reverse primer: CCC CTCGAGTCCTAATGTATATTATTTCT (XhoI) (SEQ ID NO: 29)) and orf3-orf6 (forward primer: CCC CTGCAGGGCTGTTATGAGTTTTTTAG (PstI) (SEQ ID NO: 30) and reverse primer: CCC ACTAGTCCAACGCAGCAGTGATGG (SpeI) (SEQ ID NO: 31)). A second strategy is used to remove both blpU and orf6, which is believed to encode for an immunity protein needed to protect against BlpU activity. This strategy uses the blpHR primers given above with primers designed to amplify a DNA fragment containing blpK-ISB (forward primer: CCCCTGCAGGGAAGATTTCCAATGATTG (PstI) (SEQ ID NO: 32) and reverse primer: CCC ACTAGTGGTGTACAGATGTGACTT (SpeI) (SEQ ID NO: 33)). The linear DNA molecules are cut with the specified restriction endonucleases and cloned into the integrative plasmid pKS1 (Shatalin & Neyfakh, 2005) flanking the kanamycin resistance gene. The plasmid DNA is inserted within *S. thermophilus* strain 110 (NRRL-B59671) using a standard electrotransformation protocol (Somkuti & Steinberg, 1988) with bacteria containing the plasmid identified by their ability to grow at a low temperature (30° C.) in the presence of kanamycin. A subsequent shift in temperature to 37° C. forces the integration of the entire plasmid in the bacterial chromosome via a homologous recombination event with one of the cloned DNA fragments. A shift back to the low temperature (30° C.) allows for a second homologous recombination event to occur with the other cloned DNA fragment and results in the loss of unwanted plasmid DNA and a mutant *S. thermophilus* strain 110 (NRLL-B59671), with blpU or blpU-orf6 replaced in the chromosome with the kanamycin resistance gene. This procedure is attempted several times with more than 1000 potential mutants screened; however the appropriate blpU knock out strain was not identified. Further work is needed to confirm if blpU is essential for the survival or growth of this bacterium, which would differ from previous reports on *S. thermophilus* strain LMD-9 where the blpU gene was successfully removed from the chromosome using similar cloning methods (Fontaine & Hols, 2008).

Example 5

Thermophilin 110 Activity

*S. thermophilus* strain 110 (NRRL B59671) are grown overnight in tryptone-yeast extract-lactose (TYL) medium. The overnight culture is diluted in fresh TYL medium and grown for 7 or 24 hours. At each time point, a 1 ml sample is collected. Bacterial cells are removed from the 1 ml samples by centrifugation; and the cell free supernatants (CFS) are tested for antimicrobial activity using an agar diffusion method (see Gilbreth and Somkuti (2005) and Example 2 supra). Target agar plates are prepared by inoculating molten microbiological medium with the overnight growth of susceptible bacteria (0.5% v/v; 250 µl of culture into 50 ml of medium). Target bacteria and their respective growth media are provided in Table 4 below. The inoculated molten agar is poured into square dishes and left to harden at room temperature (approximately 10 minutes). Wells are made in the solidified agar plates using a sterile glass Pasteur pipette, and each well is filled with 50 µl of CFS samples. The agar plates are stored overnight at 4° C. to allow for diffusion of the CFS into the agar medium. The agar plates with loaded wells are then incubated at 37° C. to allow for growth of the target bacterium. The agar plates are monitored for growth of the target bacterium (agar medium becomes turbid), and the presence of clear zones around wells. The clear zones demonstrate that the diffused CFS contains a component which inhibits the growth of and/or kills the targeted bacterium. Treatment of the *S. thermophilus* strain 110 (NRRL B59671) CFS with selected proteases (trypsin, papain, pronase, proteinase K, chymotrypsin) results in a loss of activity, indicating the protenaceous nature of thermophilin 110. Furthermore, antimicrobial activity is shown to be associated with a low-molecular weight peptide based on gel electrophoretic analysis (Gilbreth & Somkuti 2005). Agar diffusion assays are repeated a minimum of three times.

TABLE 4

| Target Bacterium | Growth Medium | Growth Inhibitory Activity |
|---|---|---|
| *Pediococcus acidilactici* | MRS | +++ |
| *Streptococcus pyogenes* | BHI | +++ |
| *Streptococcus mutans* | Todd Hewitt* | ++ |
| *Propionibacterium acnes* | BHI | ++ |
| *Streptococcus uberus* | TYL | + |
| *Streptococcus agalactiae* | TYL | − |
| *Streptococcus dysgalactiae* | TYL | − |
| *Lactobacillus acidophilus* | MRS | +++ |
| *Listeria innocua* | BHI | + |

+++ represents very strong growth inhibition
++ represents strong growth inhibition
+ represents mild growth inhibition
− represents no growth inhibition
*supplied by Becton Dickinson Co. (Sparks, MD)

*P. acidilactici* is used as a positive control because, in prior studies, thermophilin 110 always demonstrated very strong zones of inhibition against *P. acidilactici* (see Gilbreth and Somkuti (2005)). Data presented in Table 4 are identical for both 7-hours and 24-hours CFS samples of *S. thermophilus* strain 110 (NRRL B59671). As is evident from the data in Table 4, thermophilin 110 demonstrates very strong growth inhibitory activity against *S. pyogenes* and strong growth inhibitory activity against *S. mutans* and *P. acnes*. This data indicates that one can use thermophilin 110 or *S. thermophilus* strain 110 (NRRL B59671), which constitutively produces thermophilin 110, to prevent the growth of and/or kill these bacteria.

Example 6

Expression of BlpU (Thermophilin 110) Fusion Protein in *Escherichia coli* Strain BL21

The nucleic acid sequence (162 base pairs; SEQ ID NO: 37) corresponding to the mature BlpU peptide (not including the 23 amino acid leader peptide) is amplified from the *S. thermophilus* strain 110 (NRRL-B59671) chromosome by PCR with the primers: forward: ATA GGATCCATCGAAGGTCGTGGATGTAGCTGGGGAGGT (BamHI—recognition site underlined; nucleotides encoding the Factor Xa recognition sequence (isoleucine-glutamic acid-glycine-arginine) are italicized) (SEQ ID NO: 34) and reverse: ATCTCGAGTCACCACCAGCATGTTGCTC (XhoI—recognition site underlined) (SEQ ID NO: 35). PCR is performed using the high fidelity Pfx Taq polymerase (Life Technologies, Grand Island, N.Y.) to ensure that the DNA fragment does not have any mutations that could arise during amplification. The DNA fragment is subsequently cloned into the pGEX 6P-1 plasmid (GE Healthcare Life Sciences, Piscataway, N.J.) at the BamHI and XhoI sites. The resulting plasmid (pGEX 6P-1/blpU) encodes for a fusion protein with the glutathione S transferase (GST) tag on the N-terminus of BlpU, and expression is under control of an isopropyl β-D-1-thiogalactopyranoside (IPTG) inducible promoter. The plasmid is transformed into *E. coli* strain BL21 for recombinant expression of the fusion protein. *E. coli* strain BL21 containing pGEX 6P-1/blpU is grown overnight in Brain Heart Infusion (BHI) medium containing 100 μg/ml ampicillin. The overnight culture is diluted 1:100 into 100 ml of fresh BHI with ampicillin, and grown at 37° C. until the optical density of the culture (OD 600 nm) reaches 0.8-1.0. IPTG is added to the culture at a final concentration of 0.1 mM, and the culture is incubated for an additional 6 hours to allow for induced expression of the GST-BlpU fusion protein. Cells are then collected by centrifugation, and washed twice with phosphate buffered saline (PBS), before being resuspended in 20 ml PBS and sonicated (10 pulses of 30 seconds) to lyse the *E. coli* strain BL21 cells. The cell lysate is centrifuged to remove cellular debris, and the cell free supernatant is mixed with 1 ml bed volume of a 50% slurry glutathione Sepharose 4B resin (GE Healthcare) and incubated at room temperature for 2 hours and then 4° C. overnight. The resin, which contains the bound GST-BlpU fusion protein (~31 kDa), is collected by centrifugation, washed twice with PBS and incubated in 350 μl elution buffer (50 mM Tris-HCl, 10 mM reduced glutathione, pH 8.0) for 10 minutes. The eluent is collected after centrifugation, and dialyzed (dialysis bag with 12-14 kDa molecular weight cut off) against Factor Xa digestion buffer (20 mM Tris/HCl-100 mM NaCl-2 mM CaCl, pH 8.0) at 4° C. overnight. The eluent from the dialysis bag is recovered and analyzed by SDS-PAGE for the presence of a ~31 kDa fusion protein. The eluent is then digested with 50 μl of Factor Xa protease which releases BlpU (~5 kDa) from the GST tag (~26 kDa). The cleaved product is analyzed by SDS-PAGE for the presence of BlpU (silver nitrate staining) and antimicrobial activity against *Pediococcus acidilactici* (gel overlay method; Gilbreth and Somkuti, 2005).

SDS-PAGE analysis of *E. coli* strain BL21 with pGEX-6P-1/blpU lysate, and the eluent from the glutathione Sepharose 4B purification both show the presence of a protein band corresponding to ~31 kDa. The band corresponding to the fusion protein is not observed in lysates from the parent *E. coli* strain BL21 (without plasmid), confirming that the protein band is not an artifact. The eluent recovered after glutathione Sepharose purification does not have antimicrobial activity against *P. acitilactici*. Not wishing to be bound to a particular hypothesis, this lack of antimicrobial activity is most likely caused by the large GST tag on the N-terminus of BlpU which may prevent the bacteriocin from inserting within the target cell membrane. After Factor Xa cleavage a small peptide (~5 kDa) is observed by SDS-PAGE analysis after staining with silver nitrate, and an inhibition zone corresponding this peptide is observed when the SDS-PAGE gel is overlaid onto agar medium inoculated with *P. acidilactici* (FIG. 6). This confirms that the GST tag must be removed to render BlpU active, and that BlpU is the active bacteriocin in *S. thermophilus* strain 110 (NRRL-B59671).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim:

1. A method of inhibiting the growth of bacteria in or on an animal comprising administering an anti-bacterial composition to said animal in an amount effective to kill said bacteria, wherein said anti-bacterial composition comprises a carrier and an anti-bacterial agent,
   wherein said bacteria is *Streptococcus pyogenes*, *Streptococcus nutans*, and/or *Propionibacterium acnes*,
   wherein said anti-bacterial agent is selected from the group consisting of purified thermophilin 110, *Streptococcus thermophilus* strain 110 (NRRL B59671), and a combination thereof, and
   wherein said carrier is selected from the group consisting of a capsule, a tablet, a lozenge, a dissolvable strip, a cream, an ointment, an aqueous liquid, a non-aqueous liquid, an oil-in-water emulsion, a water-in-oil liquid emulsion, a polyol, an oil, an alcohol, a flavoring agent, a preservative, a coloring agent, microcrystalline cellulose, a granulating agent, a lubricant, a binder, a disintegrating agent, lactose, dextrose, sucrose, sorbitol, mannitol, starch, acacia gum, calcium phosphate, alginate, gelatin, calcium silicate, polyvinylpyrrolidone, cellulose, syrup, methyl cellulose, methyl hydroxy benzoate, propyl hydroxy benzoate, talc, stearic acid, magnesium, mineral oil, glycol, propylene glycol, liquid polyethylene glycol, a combination of water and at least of group selected from phenol, thymol, eugenol, eucalyptol, menthol, alcohol, chlorhexidine gluconate, cetylpyridinium chloride, hexetidine, benzoic acid, methyl salicylate, triclosan, benzalkonium chloride, methylparaben, hydrogen peroxide, domiphen bromide and fluoride, and a combination thereof.

2. The method of claim 1 wherein said anti-bacterial composition further comprises an anti-microbial agent.

3. The method of claim 1 wherein said anti-bacterial composition further comprises an immunoregulatory agent.

* * * * *